(12) United States Patent
Perez et al.

(10) Patent No.: US 6,843,593 B2
(45) Date of Patent: Jan. 18, 2005

(54) STAINING APPARATUS FOR STACKED ELECTROPHORESIS SLAB GELS

(75) Inventors: Evelio Perez, San Pablo, CA (US); Gabriela Rodriguez, Hercules, CA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 174 days.

(21) Appl. No.: 10/295,346

(22) Filed: Nov. 14, 2002

(65) Prior Publication Data

US 2004/0095846 A1 May 20, 2004

(51) Int. Cl.[7] .............................................. B01F 11/00
(52) U.S. Cl. ....................... 366/258; 366/332; 134/140; 134/158; 134/162
(58) Field of Search .......................... 366/258, 331–335; 134/140, 157, 158, 162

(56) References Cited

U.S. PATENT DOCUMENTS

| | | | | |
|---|---|---|---|---|
| 258,658 A | * | 5/1882 | Leavitt | 366/258 |
| 1,988,542 A | | 1/1935 | Coleman et al. | |
| 2,776,611 A | * | 1/1957 | Accrocco | 134/140 |
| 3,512,539 A | * | 5/1970 | Hamilton | 134/136 |
| 4,702,266 A | | 10/1987 | Chu | |
| 4,705,056 A | | 11/1987 | Chu | |
| 2002/0025278 A1 | | 2/2002 | Anderson et al. | |

* cited by examiner

Primary Examiner—David Sorkin
(74) Attorney, Agent, or Firm—M. Henry Heines; Townsend and Townsend and Crew, LLP

(57) ABSTRACT

Slab gels held on trays are agitated in a staining or fixing solution by an apparatus that includes a tray carrier that holds a stack of slab gel trays, a tank that receives the tray carrier with sufficient excess room to allow the carrier to move back and forth within the tank, and a motor with a crankpin that is connected to the tray carrier in a reciprocating connection that translates the circular path of the crankpin into a linear path of movement of the tray carrier.

7 Claims, 5 Drawing Sheets

STAINING APPARATUS FOR STACKED ELECTROPHORESIS SLAB GELS

BACKGROUND OF THE INVENTION

1. Field of the Invention

This invention lies in the field of laboratory apparatus for biochemical analyses. In particular, this invention addresses the needs of applying stains to electrophoresis slab gels used in the analysis of biochemical samples, the stains serving to permit visualization of bands on the gels that represent the components of the samples.

2. Description of the Prior Art

The widely used laboratory procedure known as gel electrophoresis utilizes the ability of solutes such as proteins, nucleic acids, and biological molecules in general to respond to an electric field by migrating through a gel across which the field is imposed, the migration occurring at different rates for different solute molecules depending on the size and charge of the molecule. A biological sample to be analyzed is placed at one end of the gel and the electric field is maintained across the gel until the solutes in the sample are separated into discrete bands distributed along the length of the gel. The location of each band defines the solute contained within that band, and in some cases, the intensity of the band serves as an indication of the amount of that solute present in the sample. Gels in the form of rectangular slabs offer the advantage of allowing several samples to be analyzed simultaneously along adjacent parallel migration paths in the same gel. Also favorable is the fact that electropherograms in slab gels are easily observed and read visually, allowing comparisons among samples and between samples and controls.

Most solutes of interest in biological samples cannot be visualized or observed either by the naked eye or by instrumentation without first being stained with a dye. It is also often necessary to fix the gel to render the gel stable for extended periods of time. Staining and fixing are time-consuming procedures, and efficiency often requires that these procedures be applied to several slab gels at the same time. For an accurate reading of the bands, the stain must be uniformly applied across any given slab gel as well as among different slab gels that are processed simultaneously.

One type of apparatus that is commonly used for staining and fixing of gels is a rocking apparatus in which the gel is placed on a rectangular tray together with the staining or fixing reagent and the tray is tipped from side to side to cause the reagent to move back and forth across the gel. Another known type of apparatus is a shaker in which the gel is again placed on a tray and the tray is shaken with a circular motion while being held horizontal. In both cases, the movement, whether rocking or shaking, is provided by a table that supports the trays and moves accordingly. The disadvantage of rocking or shaking tables is that they are bulky, expensive and consume high amounts of energy.

SUMMARY OF THE INVENTION

A self-contained apparatus has now been developed in which staining and fixing of slab gels can be performed without the use of a shaker (or rocker) table. The self-contained apparatus includes a tank, a tray carrier that fits inside the tank and is movable within the tank in a back and forth path of movement, and a motor with a reciprocating linkage that translates the rotary motion of the motor shaft to a linear oscillatory motion of the tray carrier. In certain embodiments of this invention, the apparatus further includes a tray stack to be held by the tray carrier. In a preferred embodiment of the invention, the motor is mounted to a lid that fits over and encloses the tank, the motor shaft driving a crankpin that extends into the tank interior when the lid is in place. The crankpin engages a slot in the tray carrier that is long enough to accommodate the diameter of the circle described by the circular motion of the crankpin, and the tank provides sufficient room for the tray carrier to move back and forth within the tank as the crankpin presses against the sides of the slot while rotating.

Further features, embodiments, and advantages of the apparatus will be apparent from the description that follows.

DETAILED DESCRIPTION OF THE INVENTION

While the invention can be implemented in a variety of different constructions and a with a variety of different component parts, the invention is best understood by a detailed review of a single embodiment. Such an embodiment is shown in the attached drawings and described below.

The following description makes reference only to staining and dyes for purposes of convenience. It is understood however that the invention is applicable to both staining and fixing of gels.

Figure 1:
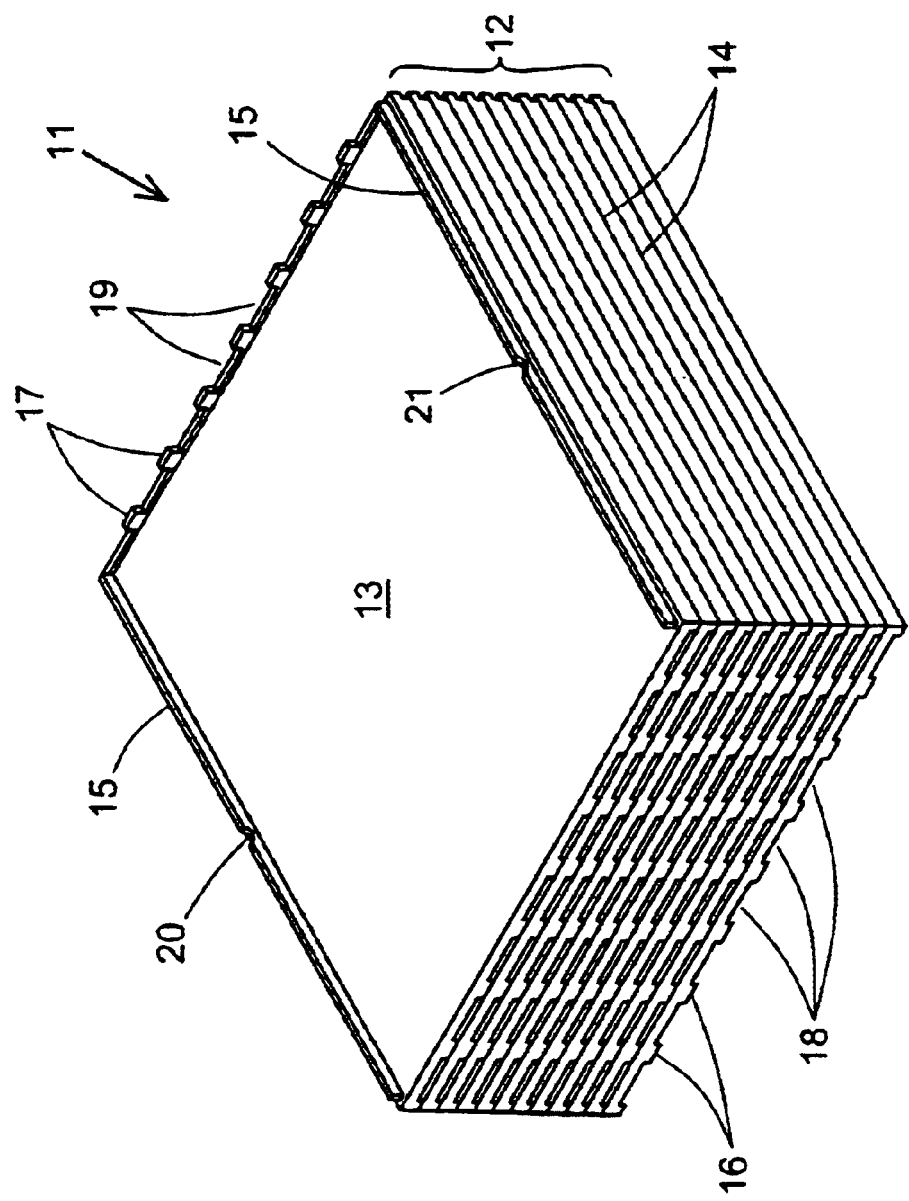
FIG. 1 is a perspective view of a stack of trays designed to hold electrophoresis slab gels.

FIG. 1 depicts one example of a tray stack that can be used in or with the present invention. The stack 11 contains twelve individual trays 12 that can be used separately or in smaller stacks of any number of such trays. Again, this is only an example—stacks of greater or lesser numbers of trays can be used as well. Each tray in the stack has a rectangular platform 13, and along two opposing side edges of the platform are downwardly extending walls 14 and upwardly extending walls 15. The upwardly extending walls 15 are located a short distance inward relative to the downwardly extending walls 14 such that the upwardly extending walls of one tray fit inside the downwardly extending walls of the tray immediately above. The result is a nested arrangement in which the nesting of the downwardly and upwardly extending walls prevents one tray from sliding relative to its neighboring trays in the direction perpendicular to the walls and establishes a gap between each pair of adjacent trays. The gap is of sufficient height to accommodate one slab gel with sufficient clearance above the gel to allow liquid to flow over the gel.

Of the two remaining side edges of the platform, one of these edges has downwardly extending feet 16 and the other has upwardly extending posts 17, each having a vertical dimension (depth or height) equal to that of the side walls. Together with the upwardly extending walls 15, the feet and posts serve as restraining barriers to hold the gel and prevent the gel from sliding off the platform. Between the feet 16 and between the posts 17 are openings 18, 19 that allow passage of the dye solution so that the solution can enter and leave the stack and flow over the gels. The feet at the front corners of the platform serve as stops for the forward ends of the upwardly extending walls 15 of the trays, and similar downward protrusions at the rear corners of the platform (not shown) serve as stops for the rear ends of the upwardly extending walls, the two sets of stops preventing sliding of the trays in the direction parallel to the walls. The feet, posts, and upwardly extending walls thus both hold the gel in place and prevent the trays from sliding relative to each other in any direction, and are simply examples of features that will perform these functions. Other features that will achieve the same or an equivalent result will be readily apparent to those skilled in the art of gel handling apparatus. Examples are pegs and holes, tabs and slots, or recesses, shoulders, flanges, and the like.

In the centers of the each of the two upwardly extending walls 15 of the top tray (and preferably each tray in the stack) are notches 20, 21 whose purpose is explained below in connection with features of the tray carrier.

Figure 2:
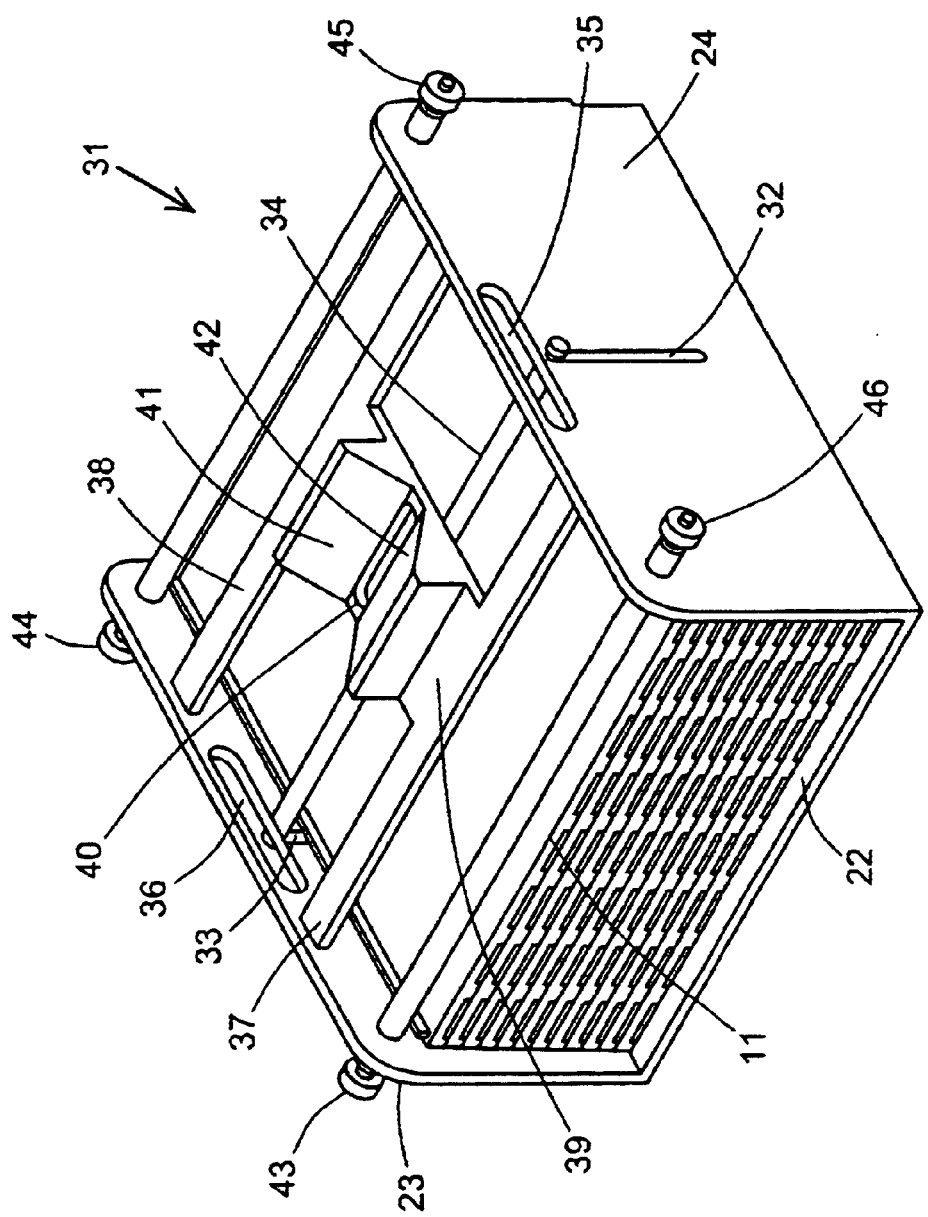
FIG. 2 is a perspective view of a tray carrier in accordance with the present invention, holding the tray stack of FIG. 1.

An example of a tray carrier 31 is shown in FIG. 2. The carrier has a floor 22 on which the tray stack 11 rests. The carrier also has two side walls 23, 24 with a vertical slot 32, 33 in each side wall. Passing between the two slots is a restraining rod 34. The restraining rod 34 engages the notches 20, 21 (FIG. 1) of the topmost tray in the tray stack to stabilize the tray stack in the carrier and prevent the stack from sliding. The slots 32, 33 allow the restraining rod to move vertically to accommodate tray stacks of different heights and hence different numbers of trays. Horizontal openings 35, 36 above the vertical slots serve as holes by which the user can grip the carrier to place it inside, and remove it from, the tank.

Spanning the top of the tray carrier are a pair of struts 37, 38 that support a web 39 with a slot 40 in its center. Upon assembly of the apparatus, the slot 40 is engaged by the crankpin of the motor, which is shown and discussed below, in a reciprocating connection that translates the circular rotary motion of the crankpin to a linear oscillatory motion of the slot 40 and hence the tray carrier. On either side of the slot 40 are sloping walls 41, 42 that slope downward toward the slot and thereby guide the crankpin into the slot 40 as the crankpin is lowered onto the tray carrier during assembly of the apparatus. Since the struts and web are rigidly fixed to the carrier and the tray stack 11 is fixed in the carrier by the restraining rod 34, the slot 40 will occupy a fixed position relative to the tray stack. Thus, movement imparted to the slot will be likewise imparted to the tray stack.

Further features of the tray carrier 31 are a set of rollers 43, 44, 45, 46 protruding outward from the side walls 23, 24. These rollers facilitate the linear oscillating movement of tray carrier in the tank, as explained below in connection with FIGS. 3 and 4.

Figure 3:
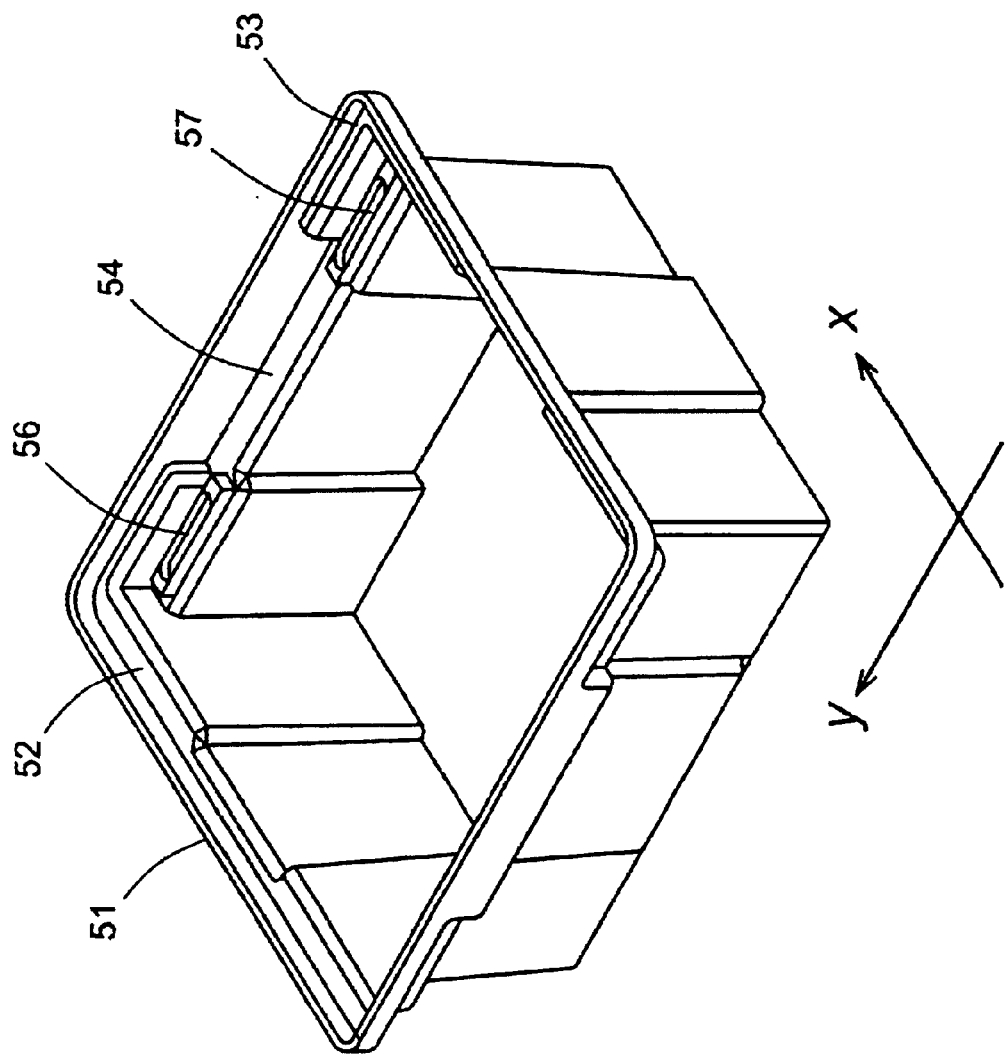
FIG. 3 is a perspective view of a tank in accordance with the present invention, designed to receive the tray stack and tray carrier of FIGS. 1 and 2.

The tank 51 is shown in FIG. 3 and is large enough to completely immerse the tray stack when the tray carrier is placed inside the tank. The longitudinal dimension of the tank (along the y axis) is large enough to accommodate the back-and-forth motion of the tray carrier. Along the rim of the tank are internal shoulders 52, 53 to support a lid (shown in FIG. 4 and discussed below). The lid and shoulders are appropriately matched in size so that the lid is not susceptible to sliding once the lid is placed on the shoulders. Below these shoulders are a second pair of shoulders 54, 55 (only one of which 54 is visible in FIG. 3 while the other 55 is visible in FIG. 4) that support the rollers 43, 44, 45, 46 on the tray carrier. One of the lower shoulders 54 contains bearings 56, 57 for the two rollers 45, 46 on one side of the tray carrier, each bearing being an elongated recess sized to receive the roller and to allow the roller, and hence the tray carrier, a range of motion along the y axis only. These bearings prevent the rollers from leaving the shoulders and restrict the movement of the tray carrier to a linear path. Although they are a preferred feature of the invention, the bearings are not a required feature since restriction of the tray carrier to a linear range of motion can be achieved by the walls of the tank itself and by other conventional features of construction that will be readily apparent to those skilled in the art. Furthermore, while four rollers are shown, with bearings for two of the shoulders, the number of rollers and bearings are not critical and can vary as well.

Figure 4:
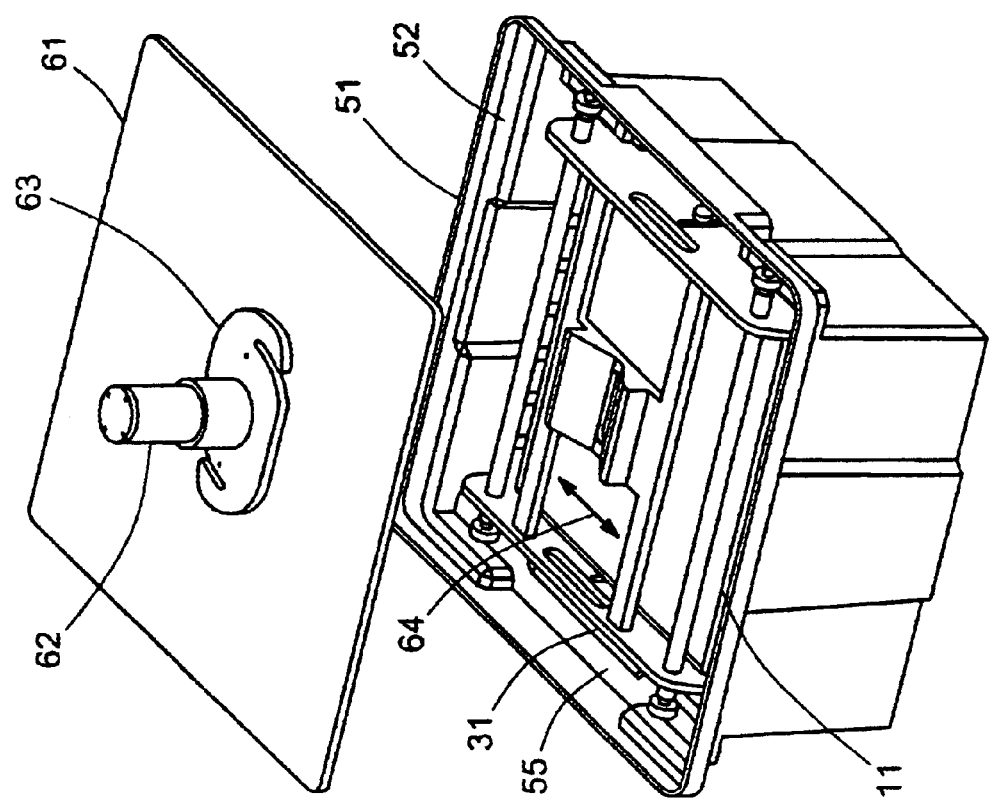
FIG. 4 is a perspective view of the tray stack, tray carrier and tank of FIGS. 1, 2, and 3, assembled with a tank lid poised above the assembly.
Figure 5:
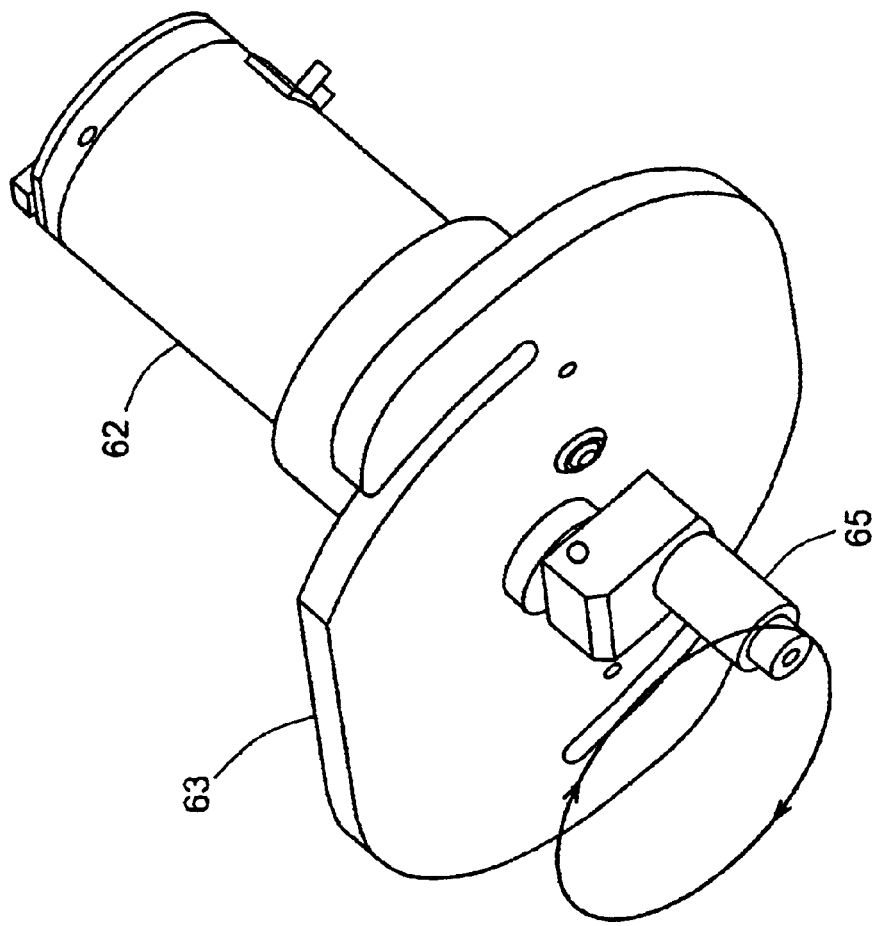
FIG. 5 is a view of the underside of a motor and crankpin that are secured to the lid shown in FIG. 4, the crankpin engageable with the tray carrier of the preceding figures.

The assembly view of FIG. 4 shows the tank 51, the tray carrier 31 inside the tank, the tray stack 11 held by the tray carrier, and a lid 61 poised above the tank. The motor 62 is secured to the lid by a motor mount 63. The direction of movement of the tray carrier 31 inside the tank is indicated by the arrow 64. FIG. 5 presents an inverted view of the motor 62 and motor mount 63. With the motor mount affixed to the lid 61 (FIG. 4), the crankpin 65 extends below the lid into the interior of the tank to enter the slot 40 in the tray carrier. The crankpin 65 is eccentric relative to the shaft of the motor and thereby follows a circular path 66 as the motor turns. The crankpin 65 includes a roller 67 to minimize friction as the crankpin contacts the rim of the slot 40.

Any motor with a rotary shaft to which a crankpin can be secured in an eccentric manner can be used. One example of such a motor is a Pittman LO-COG® DC Gearmotor, Model No. GM9413-2, available from Pittman, Harleysville, Pa., USA. This is a 12-volt motor with a no-load speed of 142 rpm and a maximum torque of 0.032 N-m.

The foregoing description is primarily for purposes of illustration. Further modifications, substitutions and variations will be apparent to those skilled in the art and are considered to be included within the scope of the invention.

What is claimed is:

1. Apparatus for agitating a plurality of electrophoresis slab gels in a liquid solution, said apparatus comprising:

a tray carrier with means for supporting a stack of trays and means for securing said stack of trays in a fixed position on said tray carrier, a tank sized to receive said tray carrier with excess internal volume to allow linear movement of said tray carrier inside said tank, and a motor with a rotary shaft joined to said tray carrier in a reciprocating connection that translates rotary motion of said rotary shaft into linear oscillating motion of said tray carrier.

2. Apparatus in accordance with claim 1 further comprising a crankpin joined to said rotary shaft and an elongated slot in said tray carrier to receive said crankpin and thereby form said reciprocating connection.

3. Apparatus in accordance with claim 2 further comprising a lid sized to cover said tank in a nonsliding closure, said motor secured to said lid such that said crankpin extends into the interior of said tank when said tank is covered by said lid.

4. Apparatus in accordance with claim 1 further comprising means for restricting movement of said tray carrier inside said tank to a predetermined linear path.

5. Apparatus in accordance with claim 4 in which said means for restricting movement comprises at least one roller on said tray carrier and a shoulder in said tank interior with an elongated bearing in said shoulder to receive said roller.

6. Apparatus in accordance with claim 1 further comprising a plurality of trays sized to fit on said tray carrier, each tray configured to support one electrophoresis slab gel while allowing liquid access to said gel.

7. Apparatus in accordance with claim 6 in which at least one of said trays has a raised rim with a notch in said rim, and said means for securing said stack of trays in a fixed position on said tray carrier comprises a rod movably mounted to said tray carrier to engage said notch, with means restricting said rod to vertical movement.

* * * * *